(12) United States Patent
Penenberg

(10) Patent No.: US 6,905,502 B2
(45) Date of Patent: Jun. 14, 2005

(54) APPARATUS FOR AND METHOD OF PROVIDING A HIP REPLACEMENT

(75) Inventor: Brad L. Penenberg, Los Angeles, CA (US)

(73) Assignee: Wright Medical Technology Inc., Arlington, TN (US)

( * ) Notice: Subject to any disclaimer, the term of this patent is extended or adjusted under 35 U.S.C. 154(b) by 0 days.

(21) Appl. No.: 10/683,008

(22) Filed: Oct. 9, 2003

(65) Prior Publication Data

US 2004/0111092 A1 Jun. 10, 2004

Related U.S. Application Data

(62) Division of application No. 10/166,209, filed on Jun. 10, 2002, now abandoned.

(51) Int. Cl.[7] .......................... A61B 12/56; A61B 17/58
(52) U.S. Cl. ............................. 606/81; 606/87; 606/91
(58) Field of Search ............................. 606/81, 86, 87, 606/91, 102, 104

(56) References Cited

U.S. PATENT DOCUMENTS

| | | | |
|---|---|---|---|
| 5,474,560 A | * | 12/1995 | Rohr, Jr. ...................... 606/91 |
| 5,743,909 A | * | 4/1998 | Collette ....................... 606/88 |
| 5,814,050 A | * | 9/1998 | Benson ....................... 606/102 |
| 6,254,605 B1 | * | 7/2001 | Howell ........................ 606/96 |
| 6,632,226 B2 | * | 10/2003 | Chan .......................... 606/102 |
| 6,695,850 B2 | * | 2/2004 | Diaz ............................ 606/91 |
| 6,702,805 B1 | * | 3/2004 | Stuart ............................ 606/1 |
| 2002/0116067 A1 | * | 8/2002 | Mears et al. ............... 623/22.4 |

* cited by examiner

Primary Examiner—Pedro Philogene
Assistant Examiner—David A Bonderer

(57) ABSTRACT

A short main incision and portal incisions at portal positions strategically displaced from the main incision are provided in a patient's hip. One portal incision (acetabular portal) provides for a disposition of reamers in the patient's acetabulum to shape the acetabulum. A cannula is inserted through the portal incision to the acetabulum and the successive reamers of progressive size are inserted into the acetabulum through the main incision to progressively size and shape the acetabulum. An approximately hemispherical acetabular component is then disposed in the prepared acetabulum to provide for hip rotation relative to the femoral component. The other portal incision (femoral portal) provides for insertion into the patient's hip of a member for driving the femoral stem into a cavity in the patient's femur. The provision of the short main incision and the portal incision minimizes the patient's loss of blood, tissue trauma, length of operating time and patient recovery time.

8 Claims, 6 Drawing Sheets

US 6,905,502 B2

APPARATUS FOR AND METHOD OF PROVIDING A HIP REPLACEMENT

This is a division of application No. 10/166,209, filed Jun. 10, 2002, now abandoned.

This invention relates to a method of providing replacement for a patient's hip with a minimal loss of blood, minimal tissue trauma and a minimal length of operating time and patient recovery time. The invention also relates to a tool which is need in the method constituting this invention.

BACKGROUND OF A PREFERRED EMBODIMENT OF THE INVENTION

Great progress has been made in the field of hip replacements. Considering that hip replacements may not even have existed a generation ago, hip replacements, particularly among the elderly, are now relatively common. In spite of the considerable progress which has been made, hip replacement operations are still relatively crude. For example, an incision of a relatively great length still has to be made in a patient's hip as one of the first steps in a hip replacement operation. The incision may be as long as approximately eight inches (8") to approximately twelve inches (12"). Such a large incision has caused patients to lose large amounts of blood and to suffer significant trauma. It has caused the length of the operation and the patient recovery time to be relatively long.

BRIEF DESCRIPTION OF A PREFERRED EMBODIMENT OF THE INVENTION

A minimal length main incision (e.g., approximately 1½"–3" long) and two portal incisions (each significantly less than 1" long) strategically displaced from the main incisions are provided in a patient's hip. A cannula is inserted through the portal incision to the acetabulum and a shaft is inserted through the cannula. A reamer is disposed through the main incision in the acetabulum and coupled to the shaft to ream the acetabulum when the shaft is rotated. Reamers of progressive size are then coupled to the shaft to progressively shape and size a socket in the acetabulum. An approximately hemispherical acetabular component is then disposed in the acetabulum to provide for hip rotation relative to the femur. The other portal (femoral portal) incision provides for a preparation of an insertion of a member into the patient's hip for preparing a femoral canal and then driving the femoral stem into a cavity in the patient's femur.

The provision of the main incision and the portal incisions minimizes the patient's loss of blood, tissue trauma, length of operating time and patient recovery time.

DETAILED DESCRIPTION OF A PREFERRED EMBODIMENT OF THE INVENTION

Figure 1:
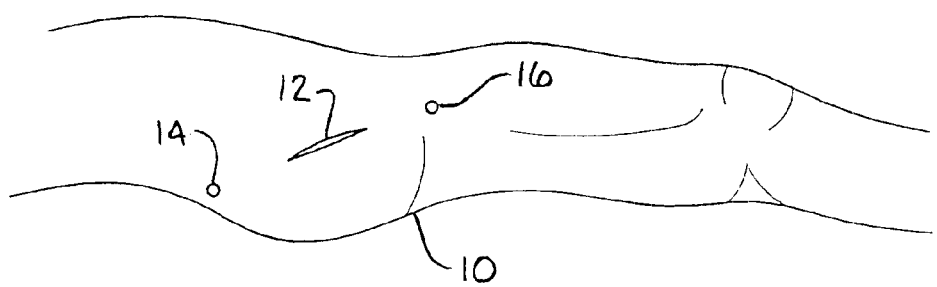
FIG. 1 is a fragmentary schematic side elevational view of a patient's hip and shows a main incision and portal incisions made in the patient's hip as an initial step in providing for a replacement of the patient's hip.

FIGS. 1–15 show progressive steps in performing a method constituting a preferred embodiment of the invention and also show apparatus included in the patentable features of the preferred embodiment of this invention. FIG. 1 schematically shows a patient's hip 10 and also shows a main incision 12 and a pair of portal incisions 14 and 16. The main incision 12 may be as short as approximately one inch (1") long. The incision 16 may be an acetabular portal incision, may be on one side of the main incision and may be significantly less than one half inch (½") in length. The incision 14 may be a femoral incision, may be on the other side of the main incision 12 from the acetabular incision 16 and may also be significantly less than one half inch (½") in length. The portal incisions 14 and 16 may be of the same approximate length.

Figure 2:
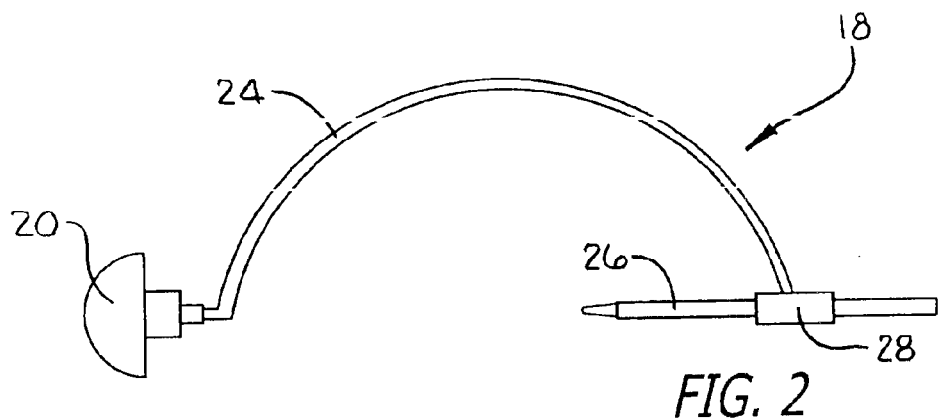
FIG. 2 is a side elevational view of a tool used by a surgeon to determine the positioning of the portal incisions in the patient's hip after the formation of the main incision in the patient's hip.

A tool generally indicated at 18 is shown in FIG. 2. The tool 18 may illustratively be used to locate the position of the portal incision 16. The tool 18 includes a positioning member 20 which may preferably have a hemispherical configuration to fit in an acetabulum 22 (FIG. 4) when the position of the acetabular portal incision 16 is being determined. A looped extension portion 24 extends from the positioning member 20. The portion 24 is preferably looped to extend through the main incision 12 to a position external to the patient's hip 10 and then to extend to a position approximating the position of the acetabular portal incision 16. It will be appreciated that the looped portion 24 may have a different configuration than that shown in FIG. 2 provided that the right end in FIG. 2 has a position corresponding substantially to that shown in FIG. 2. A marker member 26 such as a stylus attached to the looped portion at the right end of the looped portion 24 in FIG. 2. The marker member 26 is retained by a holder 28. As will be seen, the holder 28 and the marker member 26 have a substantially identical axial relationship with the positioning member 20.

Figure 3:
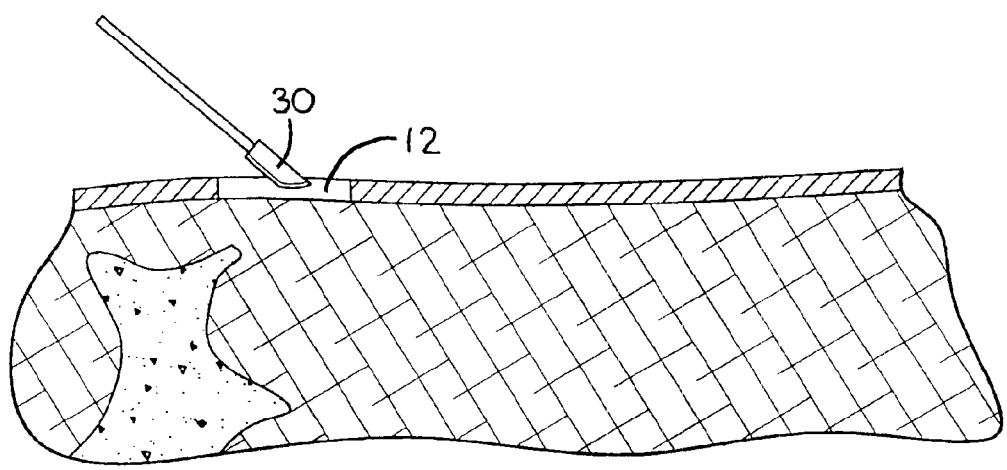
FIG. 3 is an enlarged fragmentary sectional view of a patient's hip and shows the formation of the main incision in the patient's hip.
Figure 4:
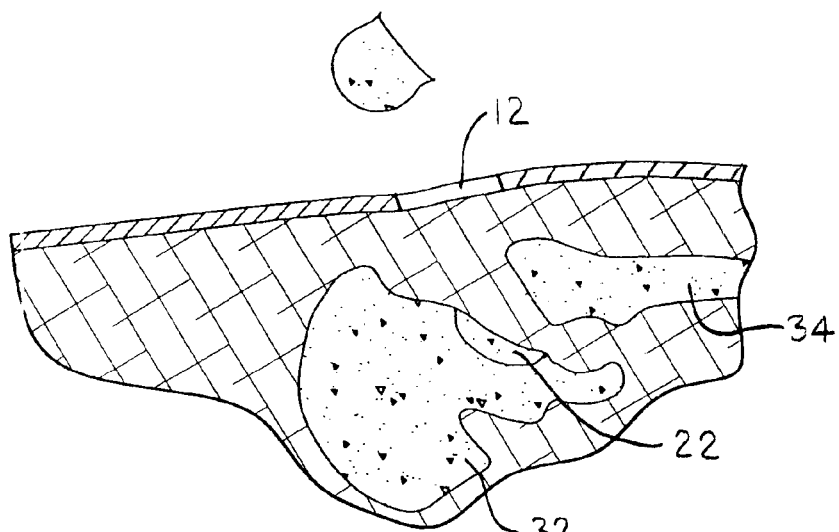
FIG. 4 is an enlarged fragmentary sectional view similar to that shown in FIG. 3 and shows the approximate positioning of the main incision in relation to a hip bone and a femur in the patient.

A first step in the performance of applicant's method is shown in FIG. 3. In this step, a cutter 30 is used to provide the main incision 12. This incision is preferably made anterior to, directly over or posterior to the greater trochanter. It will accordingly be appreciated that the positioning of the main incision 12 is somewhat discretionary. FIG. 4 is a somewhat schematic view showing the approximate positioning of the main incision 12 relative to the positioning of the patient's hip bone 32 and femur 34.

Figure 5:
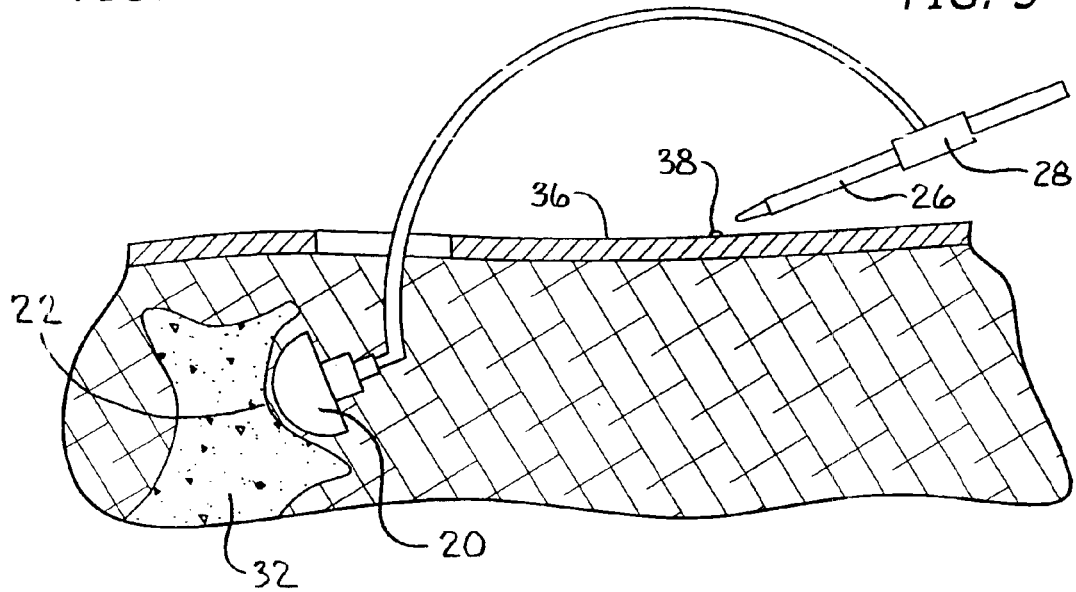
FIG. 5 is an enlarged fragmentary sectional view similar to that shown in FIG. 4 and shows the positioning of the tool of FIG. 2 in the patient's hip to determine the position of the portal incision for providing an acetabular shaping of the hip bone.
Figure 6:
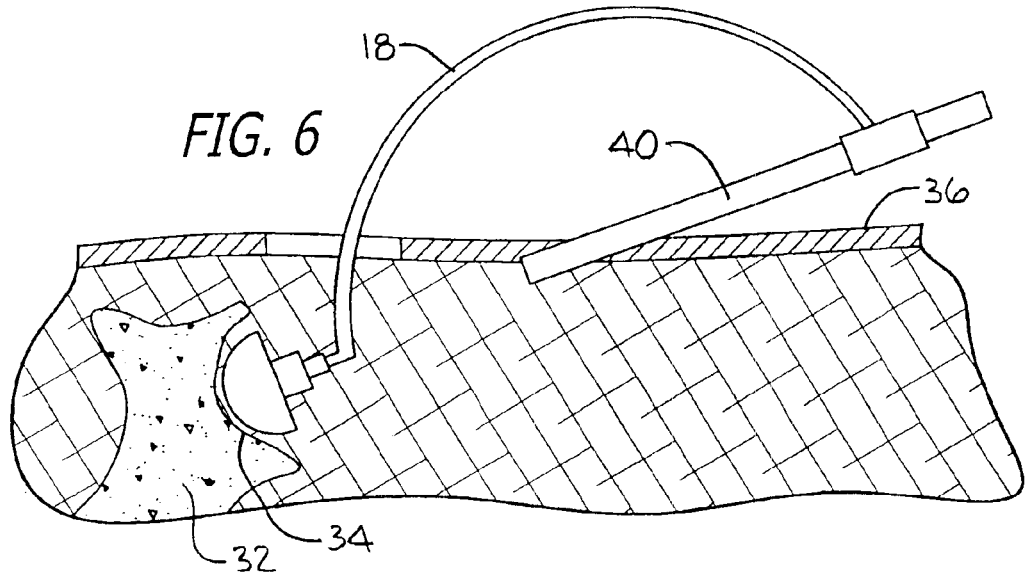
FIG. 6 is an enlarged fragmentary sectional view similar to that shown in FIG. 5 and shows partial insertion of a cannula into the patient's hip through the portal incision to provide for an acetabular shaping in the patient's hip.

FIG. 5 shows the hip bone 32 and the acetabulum 22 in the hip bone. FIG. 5 also shows the disposition of the tool 18 with the positioning member 20 in the acetabulum 22. In this disposition, the marker member 26 abuts the patient's skin 36 in the region of the patient's hip and causes a mark 38 to be produced on the patient's skin. This mark indicates the position to be provided for the acetabular portal incision 16. FIG. 6 illustrates the positioning of a cannula 40 so that it extends through the acetabular incision 16 at the mark 38 in the direction toward the axis of the positioning member 20.

Figure 7:
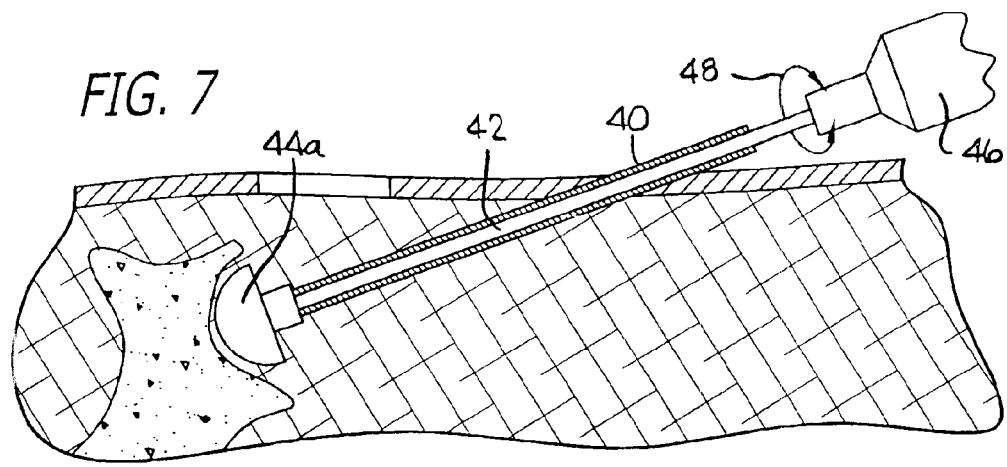
FIG. 7 is a fragmentary sectional view similar to that shown in FIGS. 5 and 6 and shows the positioning of a reamer through the cannula and the operation of the reamer to form the acetabulum in the patient's hip bone.
Figure 8:
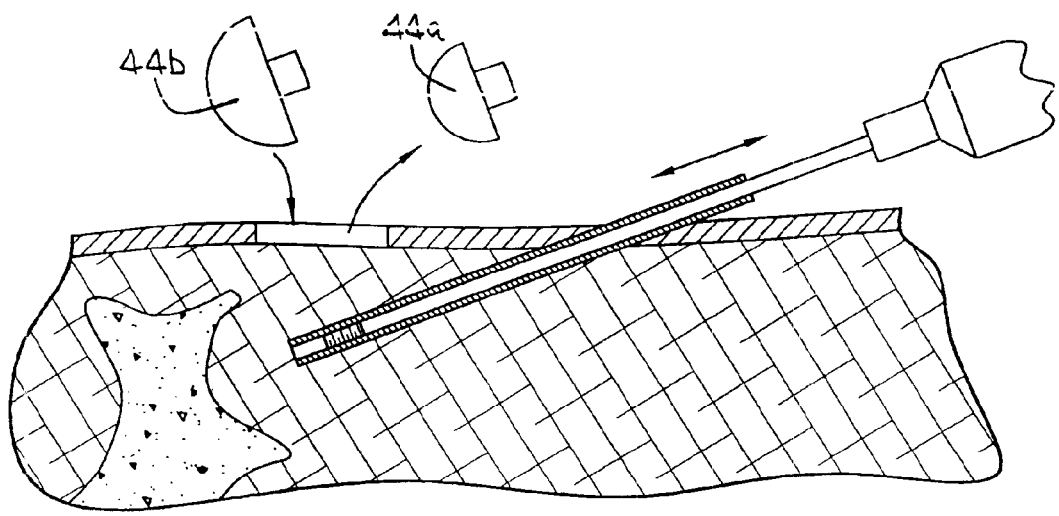
FIG. 8 is an enlarged fragmentary sectional view similar to that shown in FIGS. 5–8 and schematically shows the use of reamers of progressively increased size to shape the acetabulum in the patient's hip.
Figure 9:
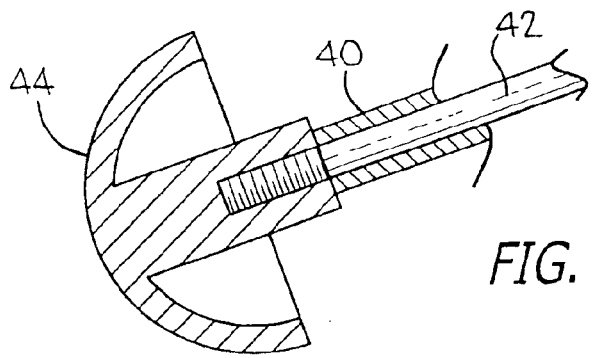
FIG. 9 is an enlarged fragmentary sectional view of one of the reamers shown in FIGS. 5–8.
Figure 10:
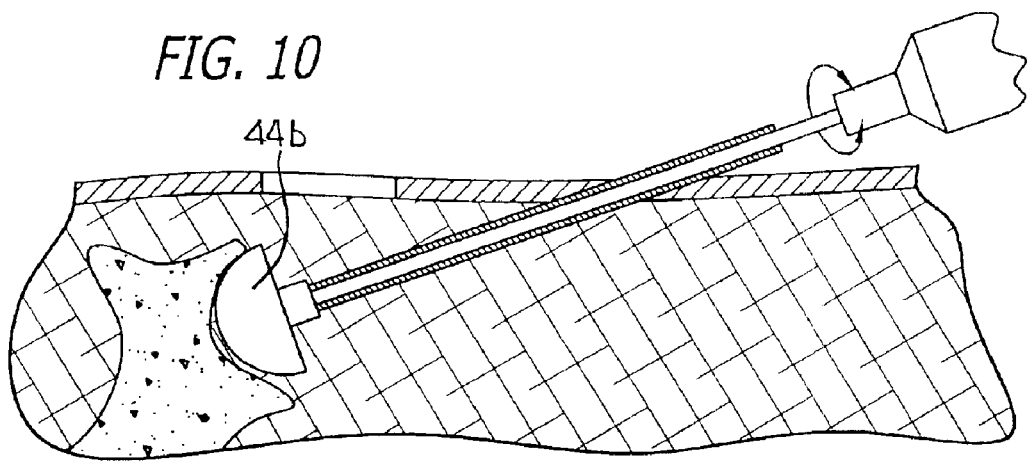
FIG. 10 is an enlarged fragmentary sectional view similar to that shown in FIG. 7 and shows a reamer which is large in comparison to the reamer shown in FIG. 7.
Figure 11:
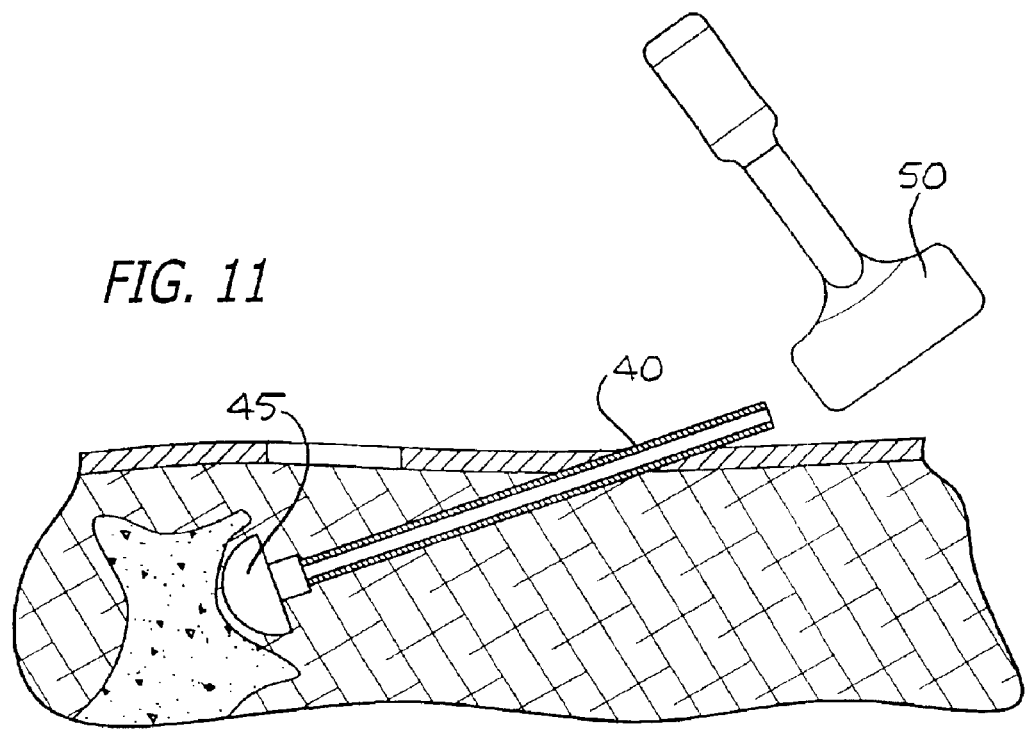
FIG. 11 is a fragmentary sectional view similar to that shown in FIGS. 5 and 6 and shows the insertion of an approximately hemispherical acetabular component into the acetabulum of the patient's hip to provide the pivotable relationship between the femoral ball and the acetabulum in the patient's hip bone.

FIG. 7 shows a shaft 42 extending through the cannula 40 and coupled to a reamer 44 which is disposed in the acetabulum 22. A motor 46 drives the shaft in one rotary direction to operate the reamer 44. The rotary movement of the shaft 42 is indicated at 48. As will be appreciated, the acetabulum 22 is sequentially reamed by reamers 44 of progressively increasing size. This is illustrated at 44a in FIG. 7 and at 44a and 44b in FIG. 8. It may also be seen by comparing the size of the reamers 44a and 44b respectively in FIGS. 7 and 10 and also in FIG. 8. When the acetabulum 22 has the desired shape, size and smoothness, a hemispherical shell (acetabular component or a trial component) 45 (FIG. 11) is introduced into the acetabulum 22 to provide a pivotal relationship with the femoral head. This may be accomplished by applying a mallet 50 to the shaft extending thru the cannula 40 as illustrated schematically at 50 in FIG. 11.

Figure 12:
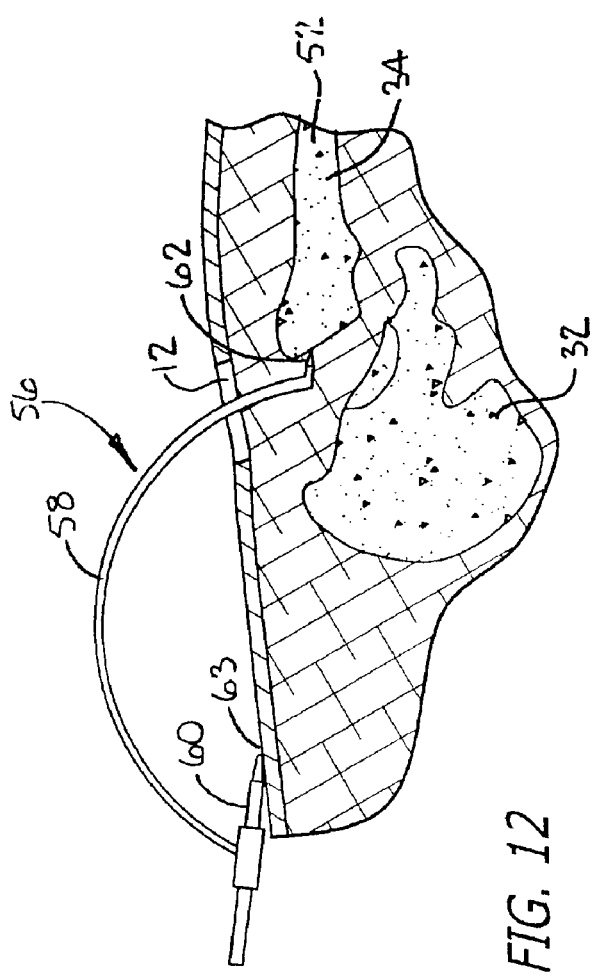
FIG. 12 is an enlarged fragmentary sectional view similar to that shown in FIG. 4 and shows the positioning relative to a femoral stem of a tool similar to that shown in FIG. 2 to determine the positioning of the portal for the femoral incision for obtaining the disposition of a femoral stem in a cavity in the patient's femur.
Figure 13:
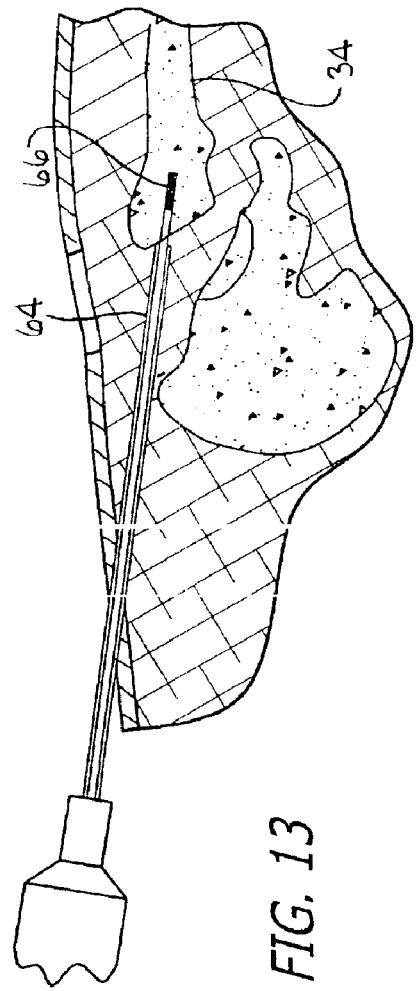
FIG. 13 is an enlarged fragmentary sectional view similar to that shown in FIG. 12 and shows the positioning of a cannula through the portal incision and the positioning of a rasp through the cannula to provide for the smoothing of the walls of the femur cavity.

FIGS. 12–15 relate to the formation of the femoral portal incision 14 and the use of this incision in connection with the disposition of the femoral stem 52 in a cavity 54 (FIG. 15) in the femur 34. As shown in FIG. 12, a tool generally indicated at 56 is provided to determine the position of the femoral portal incision 14. The tool 56 is similar in a number of respects to the tool 18. For example, the tool 56 may include an extension portion 58 and a marker member 60 respectively corresponding in configuration to the extension portion 24 and the marker member 26 in FIG. 2. The dimensions of the extension portion 58 may be different from those of the extension portion 24. The tool 56 may also be provided with a drive member 62 at the end opposite the marker member 60. The drive member 62 may have a finger configuration. The marker member 60 and the drive member 62 preferably are disposed on the same axis. When the drive member 62 is inserted into the main incision 12 and is disposed against the femoral stem 52, the marker member 60 makes a mark 63 a long scalpel blade may be passed thru this portal locator sleeve to indicate the position of the femoral portal incision 14 as shown in FIG. 12. A relatively long scalpel blade may then be passed through this portal locator sleeve.

Figure 14:
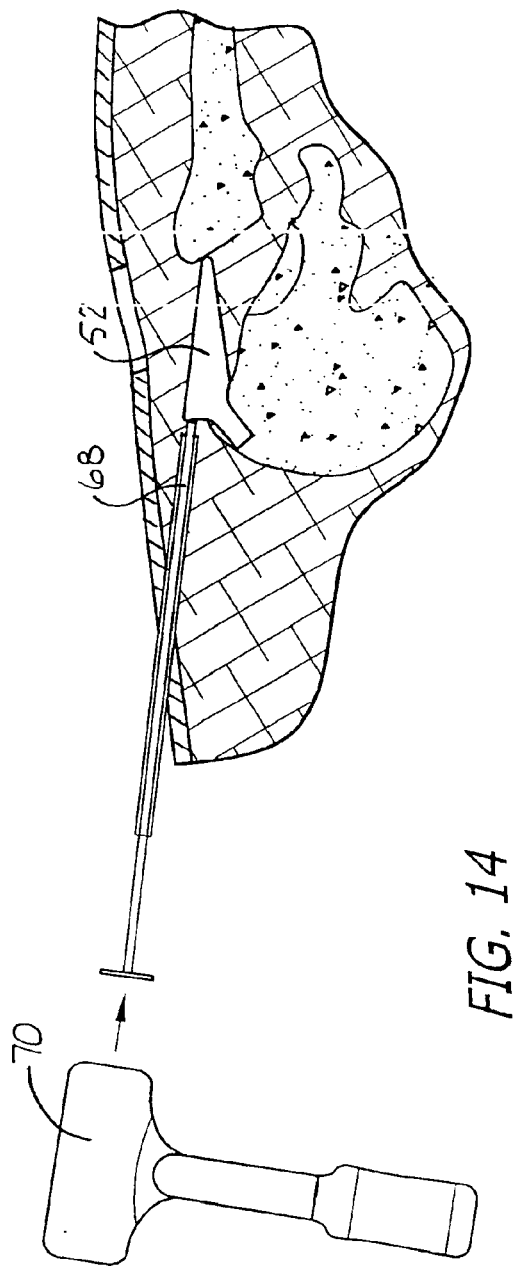
FIG. 14 is an enlarged fragmentary sectional view similar to that shown in FIG. 13 and shows how the femoral stem becomes disposed in the femur cavity.
Figure 15:
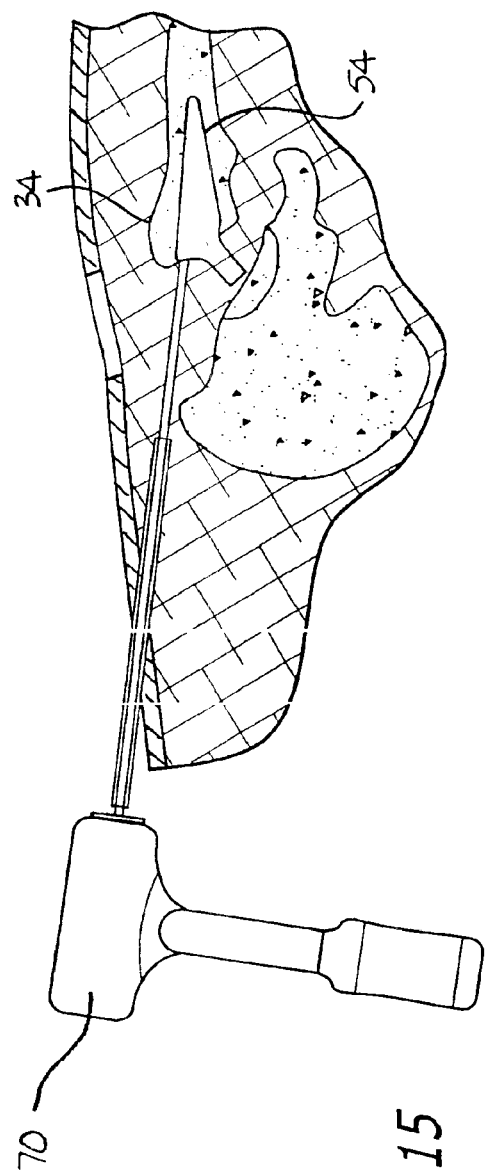
FIG. 15 is an enlarged fragmentary sectional view similar to that shown in FIGS. 13 and 14 and shows the proper disposition of the femoral stem in the femur cavity.

A cannula 64 (FIG. 13) is then inserted through the femoral portal incision 14 to a position adjacent the femoral stem 32. If soft tissues permit, a cannula need not always be used. A rasp 66 or, a reamer, a drill or a tamp is passed through the cannula 64 into the cavity 54 in the femur 34 and is operated to prepare the walls of the cavity to receive the femur. In the claims, the term "rasp" is intended to include a reamer, drill or tamp or other suitable component. The rasp 66, or, a reamer, a drill or a tamp is then withdrawn from the cannula 64 and a drive member 68 (FIG. 14) is inserted through the cannula to abut the femoral stem. This is shown in FIG. 14. A mallet 70 in FIG. 15 is then applied against the drive member 68 to move the femoral stem 52 into the cavity 54 in the femur 34. This is shown in FIG. 15.

Although this invention has been disclosed and illustrated with reference to particular preferred embodiments, the principles involved are susceptible for use in numerous other embodiments which will be apparent to persons of ordinary skill in the art. The invention is, therefore, to be limited only as indicated by the scope of the appended claims.

What is claimed is:

1. An instrument for use in locating and marking a position for a portal incision on the skin of a hip of a patient when providing for a hip replacement comprising:
    a first member positionable in the hip of the patient,
    a positioning member configured to extend at one end from the first member to a position outside of the patient's hip at a second end,
    a holder at the second end of the positioning member and a marker member in the holder the mark member disposed to make a mark on the patient's skin, the marker member being for selectively fixed in the holder at the time of formation of the mark, the mark being for use in indicating the position of a portal incision to be made on the patient's hip after the mark has been made on the patient'skin.

2. An instrument as set forth in claim 1 wherein the first member has a hemispherical shape to fit in the acetabulum of the patient.

3. An instrument as set forth in claim 2 wherein the marker member is disposed on the positioning member at an acute angle relative to the skin of the patient to mark the skin at the position of the contact of the marker member with the skin.

4. An instrument as set forth in claim 1 wherein the marker member is disposed on the positioning member at an acute angle relative to the skin of the patient to mark the skin at the position of the contact of the marker member with the skin and wherein the positioning member has a boxed configuration.

5. An instrument as set forth in claim 4 wherein the marker member includes a stylus and wherein the positioning member has a looped configuration.

6. An instrument as set forth in claim 4 wherein the positioning member has a looped configuration and wherein the marker member is disposed on the positioning member ax an acute angle relative to the skin of the patient to mark the skin of the patient and wherein the marker member is a stylus.

7. An instrument as set forth in claim 1 wherein the first member has a shape to abut the femoral stem of the patient.

8. An instrument as set forth in claim 7, wherein the marker member is disposed on the positioning member at an acute angle relative to the skin of the patient to mark the skin at the position of the contact of the marker member with the skin.

* * * * *